United States Patent
Fischer et al.

(10) Patent No.: US 7,445,295 B2
(45) Date of Patent: *Nov. 4, 2008

(54) TOOTHBRUSH AND PROCESS FOR PRODUCING SUCH A TOOTHBRUSH

(75) Inventors: Franz Fischer, Triengen (CH); Reto Strähler, Adligenswil (CH)

(73) Assignee: Trisa Holding AG, Tringen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/987,504

(22) Filed: Nov. 30, 2007

(65) Prior Publication Data

US 2008/0127439 A1    Jun. 5, 2008

Related U.S. Application Data

(62) Division of application No. 11/362,069, filed on Feb. 27, 2006, now Pat. No. 7,354,112, which is a division of application No. 10/362,590, filed as application No. PCT/CH02/00717 on Dec. 20, 2002, now Pat. No. 7,174,596.

(30) Foreign Application Priority Data

Dec. 28, 2001 (DE) .................. 101 64 336

(51) Int. Cl.
  *A46B 9/04* (2006.01)
  *A46D 3/00* (2006.01)
(52) U.S. Cl. ................... 300/21; 15/110; 15/167.1
(58) Field of Classification Search ............ 15/110, 15/167.1, 201; 300/21
See application file for complete search history.

(56) References Cited

U.S. PATENT DOCUMENTS

| 1,142,698 A | 6/1915 | Grove et al. |
| 1,191,556 A | 7/1916 | Blake |
| 1,268,544 A | 6/1918 | Cates |
| 1,796,893 A | 3/1931 | McVeigh |
| 1,908,510 A | 5/1933 | Dodson |
| 2,042,239 A | 5/1936 | Planding |
| 2,129,082 A | 9/1938 | Byrer |
| 2,139,245 A | 12/1938 | Ogden |
| 2,164,219 A | 6/1939 | McGerry |
| 2,172,624 A | 9/1939 | Romani y Robert |
| 2,263,802 A | 11/1941 | Grusin |

(Continued)

FOREIGN PATENT DOCUMENTS

CH    169 312    8/1934

(Continued)

OTHER PUBLICATIONS

Boucherie AFT Anchorless Technology Toothbrush, date unknown.

(Continued)

*Primary Examiner*—Randall Chin
(74) *Attorney, Agent, or Firm*—Oliff & Berridge, PLC

(57) ABSTRACT

The invention relates to a toothbrush having a handle and a head part, on which bristle filaments and at least one flexible cleaning element are arranged. The at least one flexible cleaning element is arranged on a carrier element, which consists of a hard material, and is connected to the head part. The invention also relates to a process for producing such a toothbrush.

29 Claims, 12 Drawing Sheets

U.S. PATENT DOCUMENTS

| | | | |
|---|---|---|---|
| 2,266,195 A | 12/1941 | Hallock |
| 2,486,847 A | 11/1949 | Hokett |
| 2,604,649 A | 7/1952 | Stephenson et al. |
| 2,614,556 A | 10/1952 | Staunt |
| 2,637,870 A | 5/1953 | Cohen |
| 2,706,825 A | 4/1955 | Blakeman |
| 2,882,544 A | 4/1959 | Hadidian |
| 2,935,755 A | 5/1960 | Leira et al. |
| 3,103,027 A | 9/1963 | Birch |
| 3,110,918 A | 11/1963 | Tate, Jr. |
| 3,129,449 A | 4/1964 | Cyzer |
| 3,177,509 A | 4/1965 | Cyzer |
| 3,230,562 A | 1/1966 | Birch |
| 3,398,421 A | 8/1968 | Rashbaum |
| 4,114,222 A | 9/1978 | Serediuk |
| 4,240,452 A | 12/1980 | Jean |
| 4,291,431 A | 9/1981 | Lewis, Jr. |
| 4,302,863 A | 12/1981 | Droeser |
| 4,429,434 A | 2/1984 | Sung-Shan |
| 4,545,087 A | 10/1985 | Nahum |
| D282,318 S | 1/1986 | Herzfeld |
| 4,633,542 A | 1/1987 | Taravel |
| 4,654,922 A | 4/1987 | Chen |
| 4,694,844 A | 9/1987 | Berl et al. |
| 4,751,761 A | 6/1988 | Breitschmid |
| 4,776,054 A | 10/1988 | Rauch |
| 4,783,874 A | 11/1988 | Perches et al. |
| 5,120,225 A | 6/1992 | Amit |
| 5,184,368 A | 2/1993 | Holland |
| 5,186,627 A | 2/1993 | Amit et al. |
| 5,228,166 A | 7/1993 | Gomez |
| 5,269,038 A | 12/1993 | Bradley |
| 5,357,644 A | 10/1994 | Theriault |
| 5,398,366 A | 3/1995 | Bradley |
| 5,435,032 A | 7/1995 | McDougall |
| 5,483,722 A | 1/1996 | Scheier et al. |
| 5,528,786 A | 6/1996 | Porat et al. |
| 5,628,082 A | 5/1997 | Moskovich |
| 5,799,354 A | 9/1998 | Amir |
| 5,802,656 A | 9/1998 | Dawson et al. |
| 5,839,148 A | 11/1998 | Volpenhein |
| 5,864,915 A | 2/1999 | Ra |
| 5,875,510 A | 3/1999 | Lamond et al. |
| 5,896,614 A | 4/1999 | Flewitt |
| 5,930,860 A | 8/1999 | Shipp |
| 5,964,508 A | 10/1999 | Maurer |
| 5,991,959 A | 11/1999 | Raven et al. |
| 6,115,870 A | 9/2000 | Solanki et al. |
| 6,151,745 A | 11/2000 | Roberts et al. |
| 6,161,245 A | 12/2000 | Weihrauch |
| 6,219,874 B1 | 4/2001 | van Gelder et al. |
| 6,290,303 B1 | 9/2001 | Boucherie |
| 6,389,634 B1 | 5/2002 | Devlin et al. |
| 6,553,604 B1 | 4/2003 | Braun et al. |
| 6,564,416 B1 | 5/2003 | Claire et al. |
| D477,465 S | 7/2003 | Reilly et al. |
| 6,702,394 B2 | 3/2004 | Boucherie |
| 6,826,797 B1 | 12/2004 | Chenvainu et al. |
| 2001/0024060 A1 | 9/2001 | Boucherie |
| 2001/0029639 A1 | 10/2001 | Seifert |
| 2001/0050507 A1 | 12/2001 | Boucherie |
| 2003/0132661 A1 | 7/2003 | Sato et al. |
| 2004/0117934 A1 | 6/2004 | Pfenniger et al. |

FOREIGN PATENT DOCUMENTS

| | | |
|---|---|---|
| DE | 558 852 | 9/1932 |
| DE | 1 210 409 | 9/1961 |
| DE | 1 883 020 | 11/1963 |
| DE | GM 75 33 143 | 2/1976 |
| DE | G 82 15 266.7 U1 | 9/1982 |
| DE | 35 29 953 A1 | 3/1987 |
| DE | 37 44 630 A1 | 7/1989 |
| DE | 39 28919 A1 | 7/1991 |
| DE | G 94 00 231.2 U1 | 5/1994 |
| DE | 198 17 704 A1 | 10/1994 |
| DE | 196 04 533 | 8/1997 |
| DE | 100 47 699 A1 | 4/2001 |
| DE | 200 06 311 U1 | 9/2001 |
| DE | 100 28 530 A1 | 12/2001 |
| EP | 0 189 816 B1 | 8/1986 |
| EP | 0 322 562 A1 | 7/1989 |
| EP | 0 405 204 A2 | 6/1990 |
| EP | 0 471 312 A2 | 8/1991 |
| EP | 0 567 672 A1 | 4/1992 |
| EP | 0 704 179 A1 | 4/1996 |
| EP | 0 972 464 A1 | 1/2000 |
| EP | 0 783 850 B1 | 3/2001 |
| GB | 1 537 526 | 12/1978 |
| JP | A-05-076416 | 3/1993 |
| JP | A 06-327517 | 11/1994 |
| JP | A 2002-010832 | 1/2002 |
| SU | 1752336 A1 | 6/1992 |
| WO | WO 94/22346 | 10/1994 |
| WO | WO 97/14330 | 4/1997 |
| WO | WO 97/14330 A1 | 4/1997 |
| WO | WO 98/01055 | 1/1998 |
| WO | WO 98/43514 | 10/1998 |
| WO | WO 99/37181 | 7/1999 |
| WO | WO 00/21406 | 4/2000 |
| WO | WO 00/30495 A1 | 6/2000 |
| WO | WO 00/47083 A1 | 8/2000 |
| WO | WO 00/53054 A1 | 9/2000 |
| WO | WO 00/60980 | 10/2000 |
| WO | WO 00-64307 | 11/2000 |
| WO | WO 00/64307 A1 | 11/2000 |
| WO | WO 00/74522 A1 | 12/2000 |
| WO | WO 00/76369 A2 | 12/2000 |
| WO | WO 01/21036 | 3/2001 |
| WO | WO 01/21036 A1 | 3/2001 |
| WO | WO 01/87101 A2 | 11/2001 |
| WO | WO 02/05679 A1 | 1/2002 |
| WO | WO 02/11583 A2 | 2/2002 |
| WO | WO 02/38004 A1 | 5/2002 |
| WO | WO 03/043459 | 5/2003 |
| WO | WO 03/043459 A2 | 5/2003 |

OTHER PUBLICATIONS

Signal Toothbrush, date unknown.

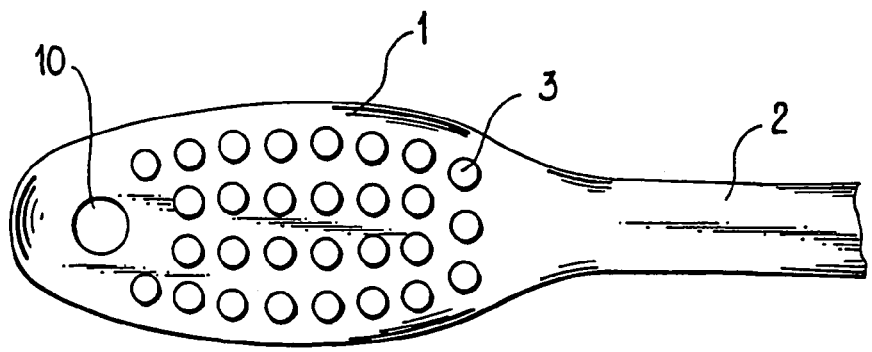
Fig. 3a
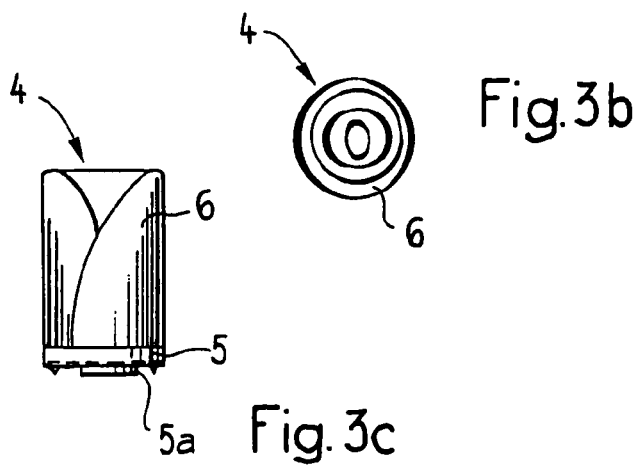
Fig. 3b
Fig. 3c
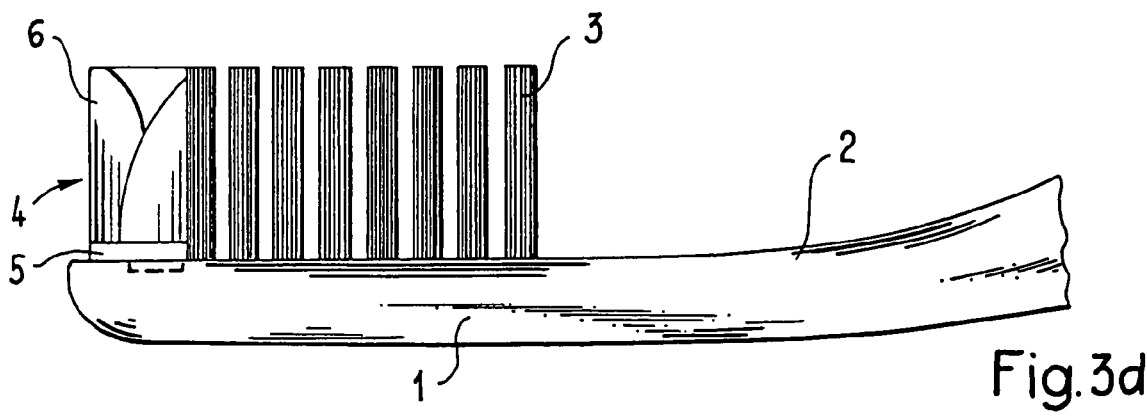
Fig. 3d
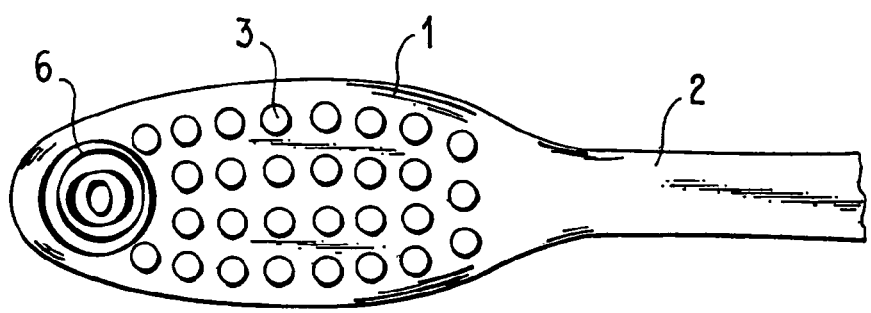
Fig. 3e

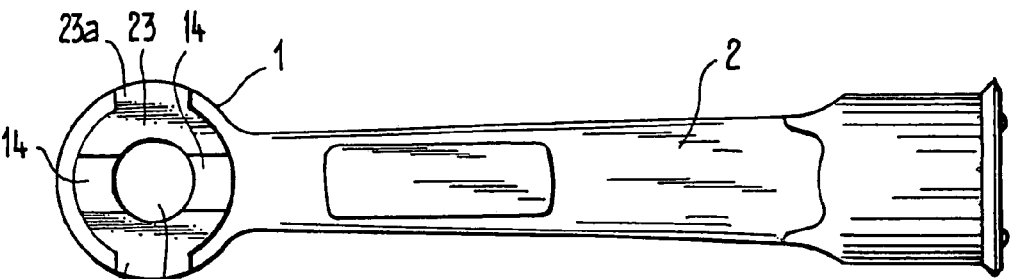
Fig. 6a
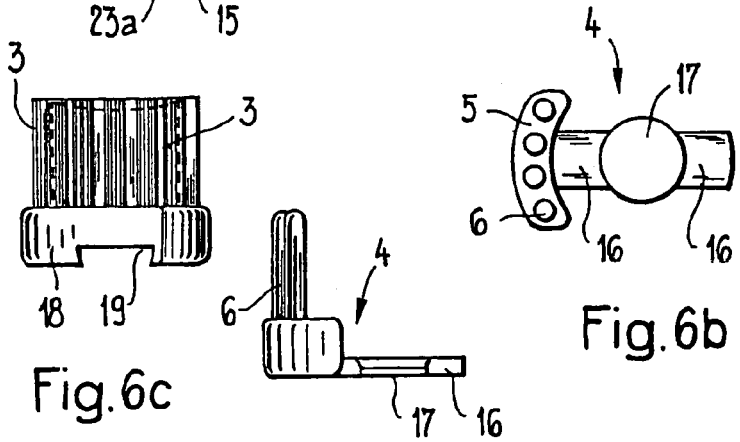
Fig. 6b
Fig. 6c
Fig. 6d
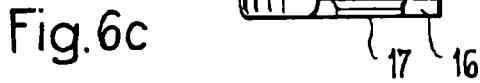
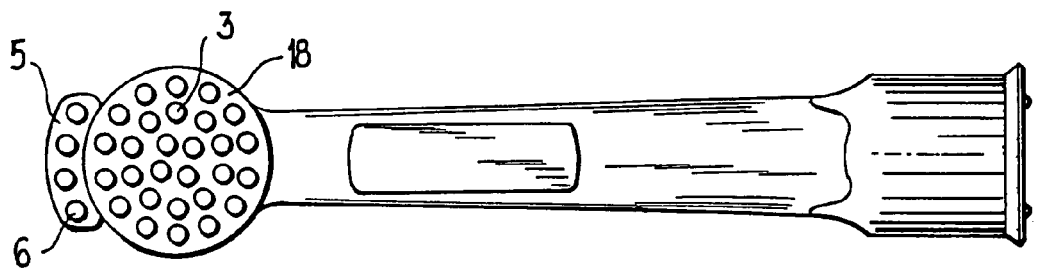
Fig. 6e
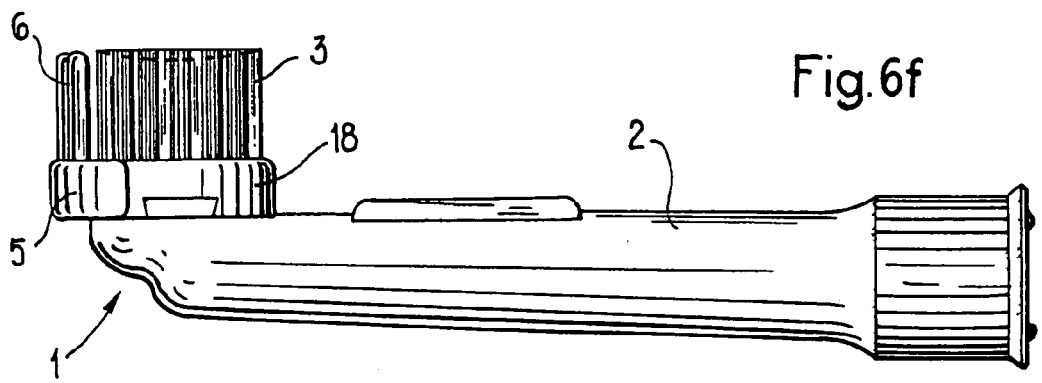
Fig. 6f

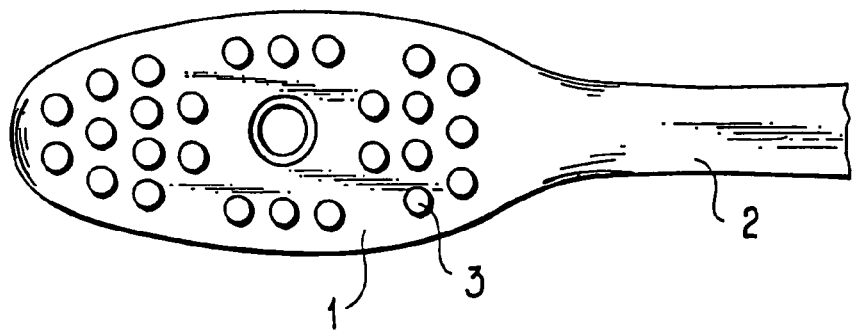
Fig.8a
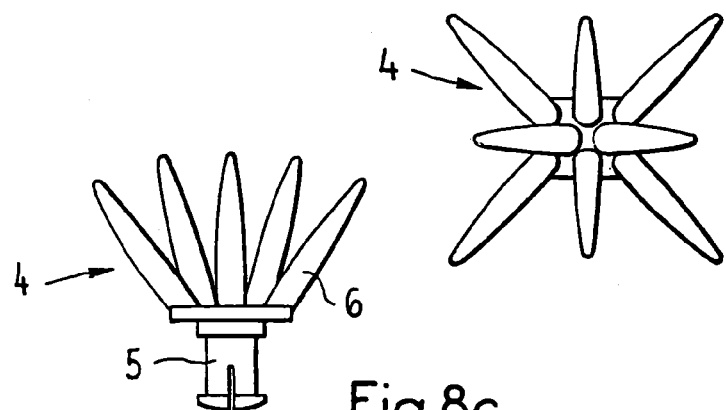
Fig.8b
Fig.8c
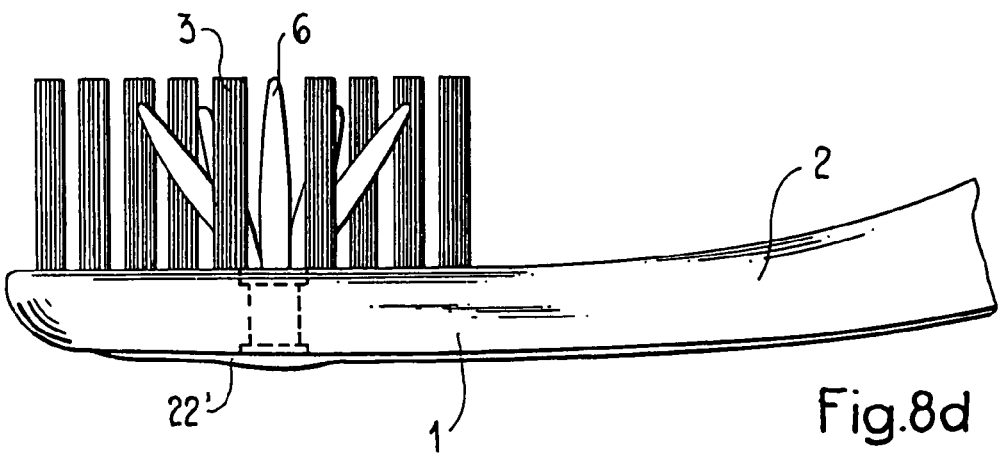
Fig.8d
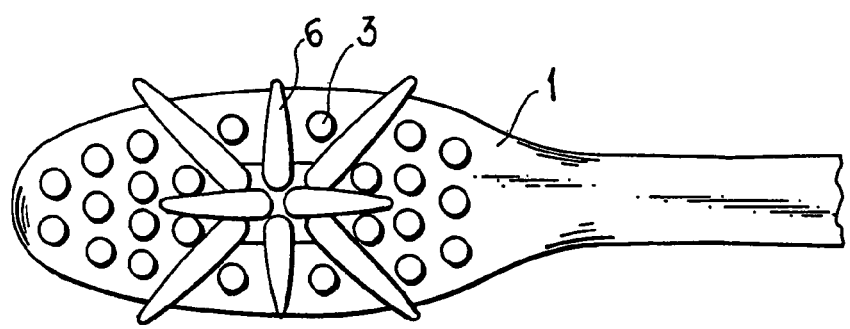
Fig.8e

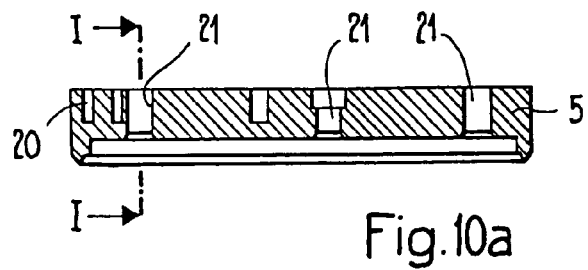
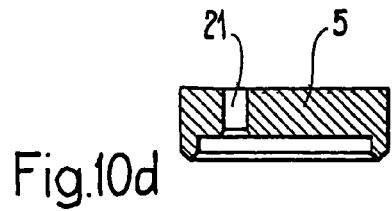
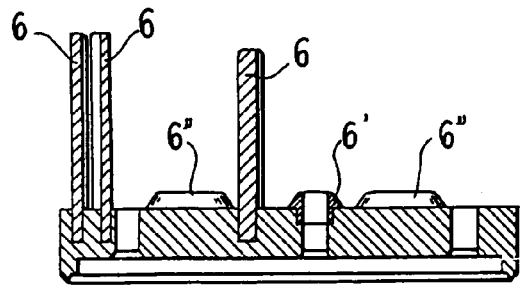
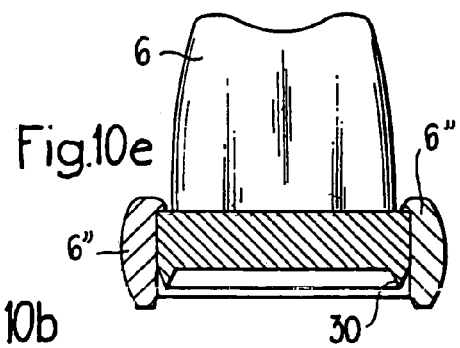
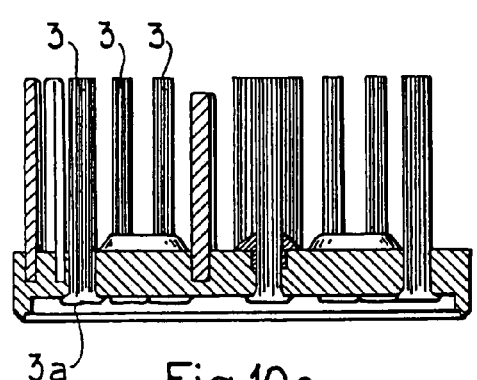
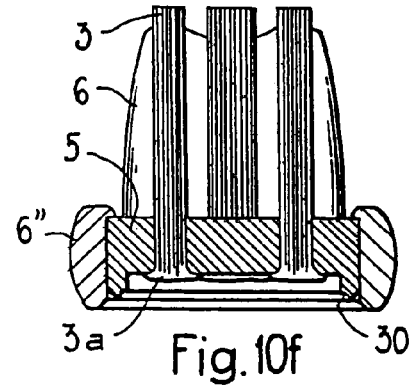
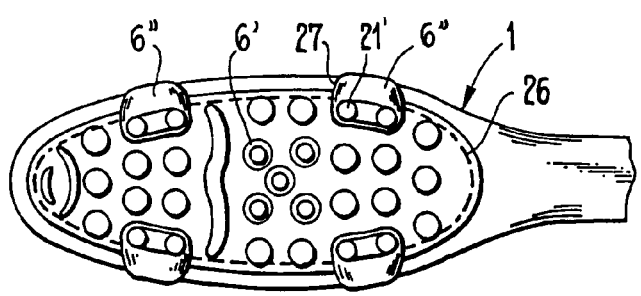
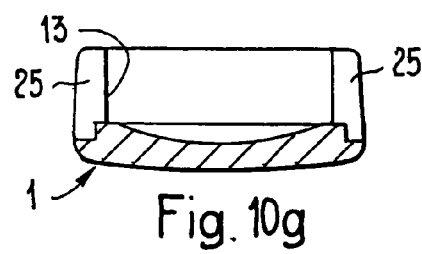
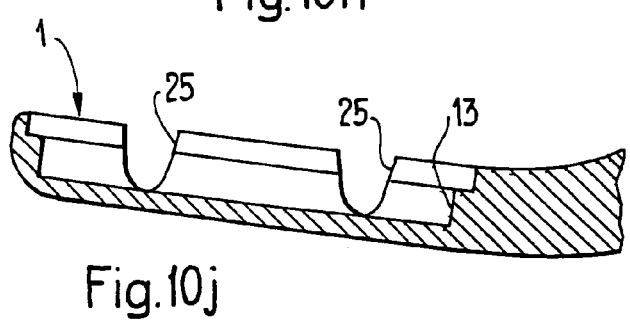
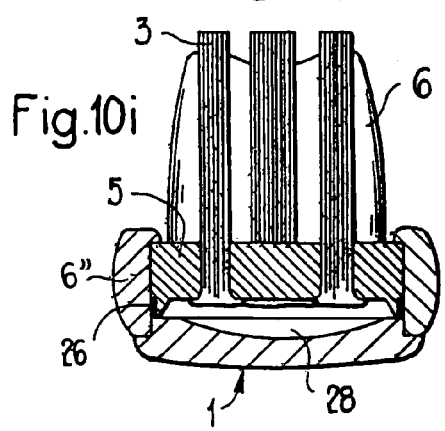

TOOTHBRUSH AND PROCESS FOR PRODUCING SUCH A TOOTHBRUSH

CROSS-REFERENCE TO RELATED APPLICATIONS

This is a Division of application Ser. No. 11/362,069 filed Feb. 27, 2006, which is a Division of application Ser. No. 10/362,590 filed Mar. 17, 2003, which in turn is a National Stage of PCT/CH02/00717 filed Dec. 20, 2002, which claims the benefit of German Patent Application No. 10164336.5 filed Dec. 28, 2001. The entire disclosure of the prior applications is hereby incorporated by reference herein in its entirety.

BACKGROUND

The invention relates to a toothbrush and for a process which is intended for producing the same.

Toothbrushes with a conventional bristle arrangement comprising clusters of bristle filaments, e.g. made of a polyamide (PA) or polyester (PBT), and an additional flexible structure are known, for example, from WO 00/64307 and WO 01/21036. The conventional bristles here serve for customary teeth-cleaning purposes, while the flexible structure can perform different functions, e.g. massaging the gums, damping the cleaning movement, removing plaque, polishing the tooth surface, suspending the bristles in an elastic manner and/or sealing non-welded locations. WO 00/64307 discloses a toothbrush with rod-like flexible cleaning elements which are of approximately the same length as the conventional clusters of bristles and are arranged on the periphery of the head part of the toothbrush. In the case of WO 01/21036, elastic cleaning elements are of sheet-like, e.g. undulating, configuration and are arranged within the conventional bristle arrangement. In the case of WO 00/64307, a plurality of the flexible cleaning elements are connected to one another via a material bridge made of the same material.

SUMMARY

Following the operation of covering the head part of the toothbrush with conventional bristles, the cleaning elements are produced by virtue of the head part being encapsulated by injection molding. The disadvantage here is that the bristle filaments have to be prepared for use, e.g. by virtue of the clusters of bristles being rounded or a predetermined profiling being produced, before the flexible structure is produced. Renewed insertion into the injection mold is then necessary in order to produce the flexible structure. It is possible here for the clusters of bristles to be damaged or contaminated. The elastic-structure shapes which it is possible to produce are limited, inter alia, for demolding reasons.

The object of the invention is to provide a toothbrush, with conventional bristles and a flexible structure, which is straightforward to produce. The intention is also to specify a corresponding production process.

According to the invention, in the case of a toothbrush of the type mentioned in the introduction, at least one flexible structure, e.g. a cleaning element, is arranged on a carrier element which consists of a hard material. This carrier element is connected to the head part. Such a toothbrush has production-related advantages since the additional part, i.e. the carrier element provided with the flexible structure, can be produced separately and straightforwardly connected to the head part.

The connection between the carrier element and the head part may be produced mechanically by clamping or snap-fitting or riveting, chemically by adhesive bonding, by ultrasonic welding, or thermally by welding or other methods of supplying heat. It is preferred, in terms of production, for the carrier element to consist of the same material as the head part since, in this case, only one hard component need be provided for producing the brush and there is no need to ensure material compatibility. This is advantageous, in particular, for ultrasonic welding.

The arrangement of the flexible structure on a carrier element consisting of a hard material has the following advantages: the additional part may be produced, and prepared for use, separately from the rest of the toothbrush body, comprising the handle and head part. In a straightforward further step, the carrier element is connected to the head part, it being possible to use any of the abovementioned connecting methods and the hard carrier element preferably being formed in adaptation to the head part. The carrier element may be formed, for example, such that, during the later connecting step, it engages around the head part in a clamping manner. On account of the hard carrier element, the additional part is easy to handle and can be gripped considerably more easily than an additional part produced entirely from a flexible material.

The additional part is small in comparison with the rest of the toothbrush. The necessary molds are thus also small and cost-effective. The basic toothbrush body and the bristle covering may be produced using a standard mold even if they are later provided with different additional parts. In order to produce toothbrushes with different additional parts, all that is necessary is to exchange the additional part and/or the corresponding mold therefor, which can be done in a straightforward and cost-effective manner.

A further advantage of producing the additional part and basic body separately is that it is possible to realize any desired shapes of flexible cleaning elements, e.g. even those which cross over the conventional bristles, come into contact therewith or displace the same when the additional part is inserted. The separate production does not pose any problems for the demolding of the flexible structure. It is possible to produce geometries by injection molding which would be extremely difficult to demold if the cleaning element were fitted directly on the bristle-covered head part.

Up until now, the flexible structure, for production-related reasons, has been produced from the same material as any flexible components on the handle part. The invention provides a greater degree of freedom for the material of the structure, with the result that it is possible to use, for example, a different degree of hardness.

A non-releasable connection between the additional part and the head part prevents the additional part from detaching during use and eliminates the risk of swallowing.

The conventional bristles are fastened, for example, directly on the head part, on a bristle plate acting as a further carrier element, or also on the carrier element for the flexible cleaning elements, all variants having advantages. During the operation of fastening the bristles on the head part or on the bristle plate, the flexible structure and the conventional bristles may be prepared independently of one another for later use before the head part and additional part are assembled, with the result that they do not damage or contaminate one another.

The conventional bristles, in both cases, may be prepared for use before or after the flexible structure is fitted. If the two components are provided on the carrier element, it is preferable first of all for the flexible structure, including any cleaning elements, to be integrally formed and then for the carrier element to be covered with bristles, which may be guided, for example, through cutouts in the soft or hard component.

Producing the additional part, i.e. the carrier element with one or more flexible cleaning elements, preferably takes place by two-component or multi-component injection molding. In this case, a non-releasable connection is preferably produced between the components.

The flexible structure is preferably also arranged, e.g. molded, laterally on the carrier element, in which case, in the assembled state, it terminates laterally with the outer contour of the head part or projects beyond the same. It serves, for example, for sealing non-welded locations, for massaging the gums, e.g. by way of molded-on elastic elements which project slightly, or as impact protection during cleaning.

The flexible cleaning element preferably consists of an, in particular, thermoplastic elastomer, e.g. of natural or synthetic rubber. The material used for the basic toothbrush body is preferably used for the carrier element, in particular polypropylene, styrene-acrylonitrile, polyester, acrylonitrile-butadiene-styrene (ABS) or a polyurethane such as Isoplast®. The Shore A hardness of the soft component is preferably less than 90 and particularly preferably below 50.

The carrier element is particularly preferably covered with bristles by AFT (Anchor Free Tufting) technology. In this case, first of all, the hard-material carrier plate is produced with the flexible structure, in particular by two-component injection molding. Then, the bristle filaments are guided through cutouts in the carrier plate and/or in the flexible structure and, for fastening on the carrier plate and/or the flexible structure, are welded or adhesively bonded by way of their rear ends, which in the application case are directed toward the brush head. This has the advantage that it is possible to realize largely any desired bristle arrangements, in particular even sheet-like bristle structures. The carrier element is connected to the head part, in particular, by means of ultrasonic welding, e.g. as is described in DE 200 06 311 U.

Since elastomeric material, in particular a thermoplastic elastomer, on account of the pronounced damping of the ultrasonic vibrations, can only be welded ultrasonically to a limited extent, the welding surface between the carrier element and head part is preferably kept at least partially free of the flexible component. For this purpose, the injection point of the soft component is preferably selected to be on the bristle-carrying side of the carrier element, in order that no material bridges from the soft component reduce the size of the welding surface. However, for the case where flexible elements are intended to be arranged in the region of the welding surface, they are preferably positioned to the side of the longitudinal axis of the toothbrush. This likewise produces non-welded locations laterally on the carrier element, while it is possible to weld the longitudinally front and rear regions between the carrier element and head part. This ensures that the carrier element is held well since the front and rear regions, in particular, and, to a lesser extent, the side regions, are subjected to loading by the cleaning movement and the corresponding leverages. Merely punctiform welding with non-welded locations may also be used specifically, in order that the brush head and carrier element can be moved in relation to one another and a certain level of flexibility of the brush head as a whole is thus achieved.

It is also possible for the flexible structure, in the manner of a sealing lip, to serve for the additional sealing of non-welded locations. As a result, the space between the carrier element and the head part is advantageously sealed against the ingress of water. It is thus not possible for any germs to accumulate in this region, and the brush is more hygienic. In order to achieve a reasonable sealing function, the Shore A hardness of the software component is preferably less than 50.

BRIEF DESCRIPTION OF THE DRAWINGS

Examples for the invention are described hereinbelow and illustrated in the drawings, in which, purely schematically:

FIGS. 3a-e show views of a toothbrush of which the additional part is fastened by welding;

FIGS. 6a-f show views of a toothbrush in the case of which the additional part is fastened in a clamping manner;

FIGS. 8a-e show views of a further toothbrush of which the additional part is fastened by a snap-fitting connection;

FIGS. 10a-j show the production of a further toothbrush by AFT; and

DETAILED DESCRIPTION OF EMBODIMENTS

Figure 1A:
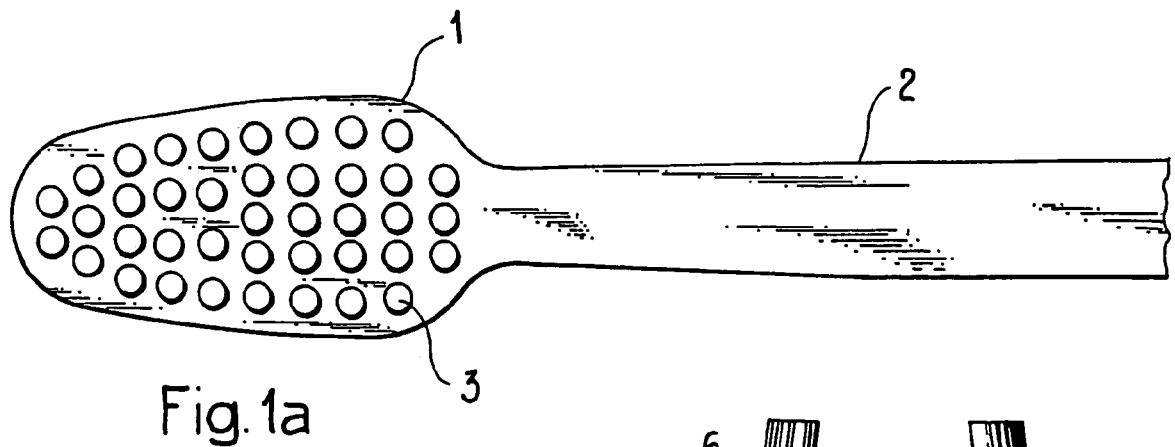
FIGS. 1a-d show views of a toothbrush according to the invention in various assembly stages, the additional part being fastened on the head part by riveting.
Figure 1B:
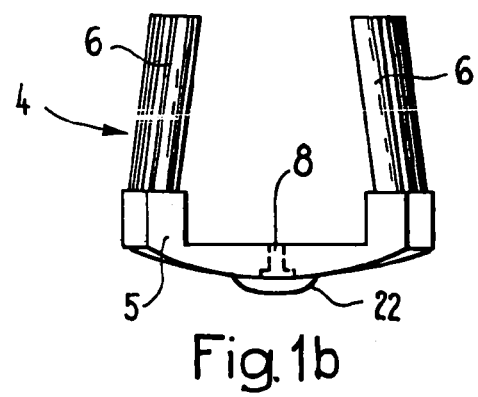

All of the toothbrushes illustrated have a basic body with a head part 1 and a handle part 2, which is only partially illustrated. An additional part 4 with a plurality of flexible cleaning elements 6 of different shapes, which are connected to a carrier element of likewise different shapes, is connected to the head part 1 when the toothbrush is in the finished state. The head part 1, furthermore, is provided directly (FIGS. 1-5) or indirectly (FIG. 6) with clusters 3 of conventional bristle filaments. The materials and arrangements of the clusters of bristles 3 may vary. It is only the special features of the individual exemplary embodiments which are discussed hereinbelow, and elements which correspond to one another are provided with the same designations.

FIGS. 1a and c show a toothbrush of which the head part 1 has already been provided with clusters of bristles 3. The additional part 4 illustrated in FIG. 1b has a sectionally U-shaped carrier element 5 made of a hard material, in particular the same plastic which has been used for producing the head part 1 and/or the entire basic body. Flexible cleaning elements 6, in this case in the form of straight rods, are firmly connected to the carrier element 5. The cleaning elements 6 are inclined slightly out of the vertical, toward one another, and enclose an angle of from 5 to 30° with the vertical. In this way, the elastic cleaning elements 6 come into contact with the conventional clusters of bristles 3 (FIG. 1d) and may even cross over (not illustrated) the latter. Using conventional production processes, such a position can only be realized with high-outlay displacement methods.

Figure 1C:
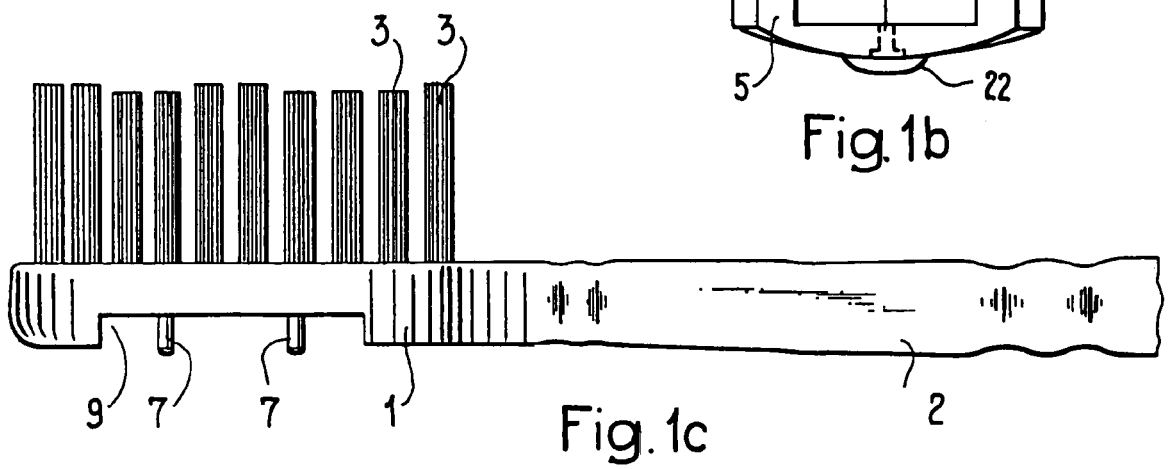
Figure 1D:
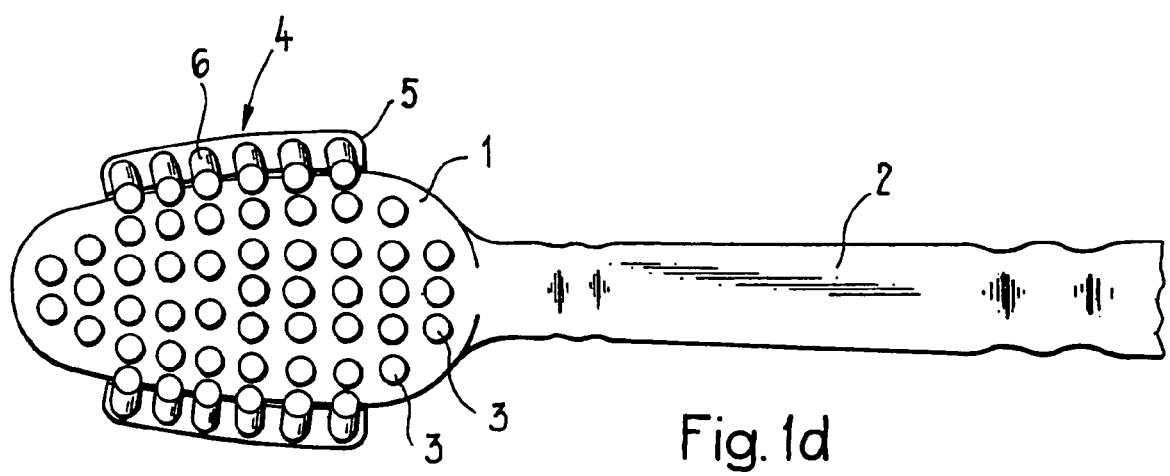

The carrier element 5 is adapted in shape to a cutout 9, visible in FIG. 1c, in that region of the head part 1 which is directed away from the clusters of bristles 3. Also located in this region are pins 7, which can be plugged through a hole 8 in the carrier element 5. The pins 7 are cold-formed or hot-formed and thus permanently fixed in the hole 8. FIG. 1d shows a plan view of the finished toothbrush.

Figure 2A:
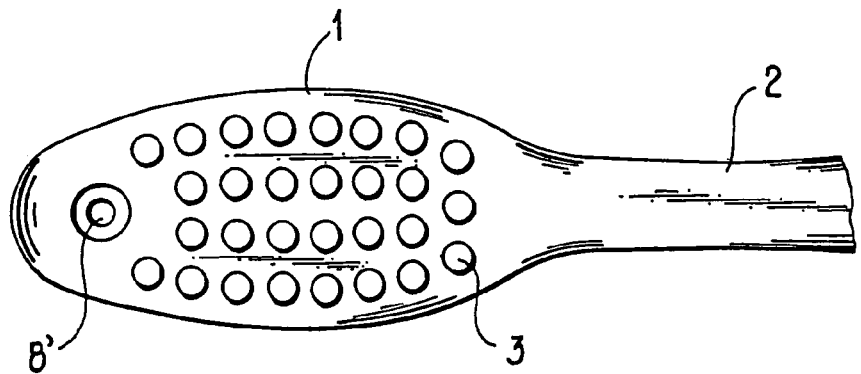
FIGS. 2a-e show views of a further toothbrush of which the additional part is fastened by riveting.
Figure 2B:
Figure 2C:
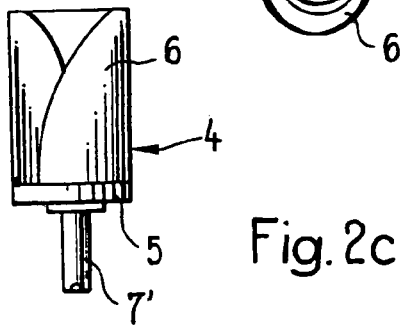
Figure 2D:
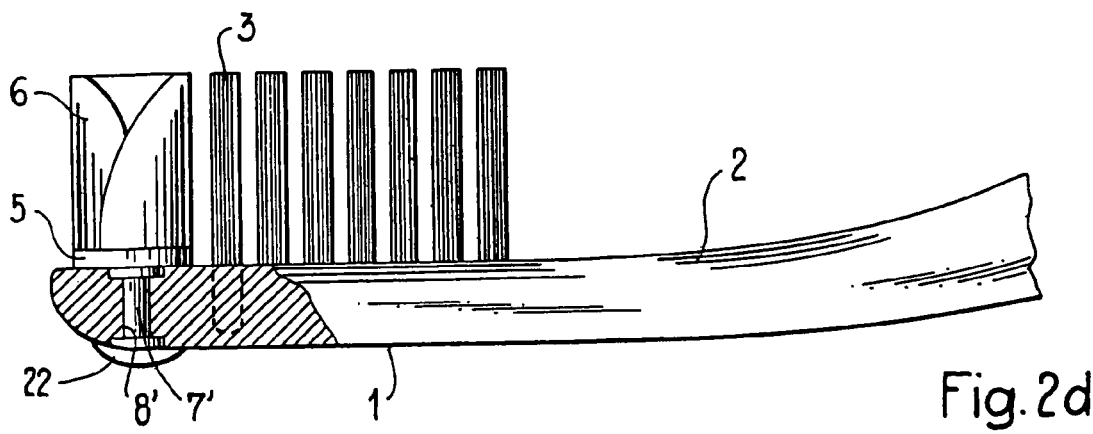
Figure 2E:
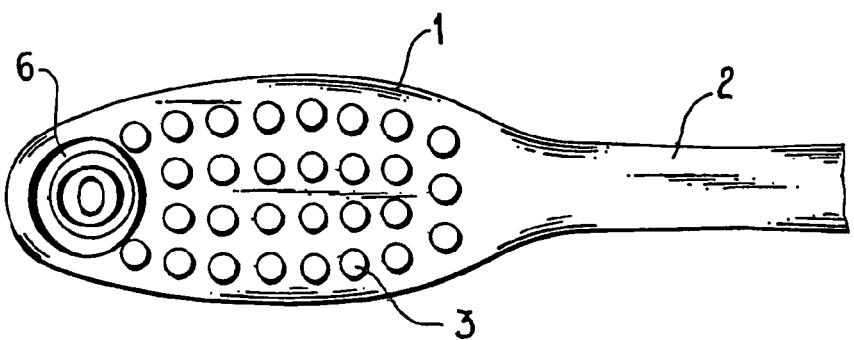

For reasons of esthetics or hygiene, the bottom region of the hole 8 or of the head part 1 as a whole may be covered by a protective layer 22 made of soft plastic (cf. FIG. 2d). The boundary regions between the carrier element 5 and the head part 1 are likewise preferably covered by soft plastic. An example of the material used for this purpose is the soft material which is also used for the handle region of the toothbrush. The protective layer is preferably molded on during the production of the handle part by multi-component injection molding. It is also possible, however, for the plastic layer to be integrally formed directly on the carrier element.

A further example of a toothbrush of which the additional part 4 is connected to the head part 1 by riveting is illustrated in FIGS. 2a-e. The additional part, in this case, comprises a plate-like carrier element 5 to which sheet-like flexible cleaning elements 6 are connected in the form of a rosette. The carrier element 5 has a pin 7' by means of which the additional part 4 can be plugged through a correspondingly prepared hole 8' in the front end of the head part and can be fixed by virtue of the pin 7' being deformed. The flexible cleaning elements 6 are located in the region of the tip of the head part 1. The bristle arrangement with individual clusters of bristles 3 follows in the direction of the handle part 2. A protective layer 22 covers the region of the hole 8'.

FIGS. 3a-e show a further example of a toothbrush, which ends up similar to a toothbrush according to FIG. 2. The additional part 4 with a plate-like carrier element 5 and rosette-like flexible cleaning elements 6, in this case, is connected to the head part 1 by welding. For this purpose, the front region of the head part has a plate-like cutout into which the carrier element 5 is permanently introduced, by way of a correspondingly structured underside 5a, by means of ultrasonic welding. FIG. 3d shows a side view of the finished toothbrush, and FIG. 3e shows the plan view of the combined bristle arrangement comprising conventional clusters of bristles 3 and flexible cleaning elements 6.

Figure 4A:
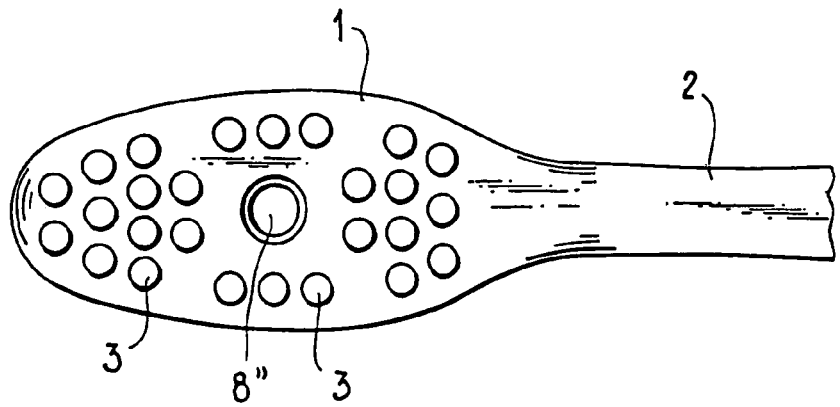
FIGS. 4a-e show views of a toothbrush of which the additional part is fastened by means of a snap-fitting connection.
Figure 4B:
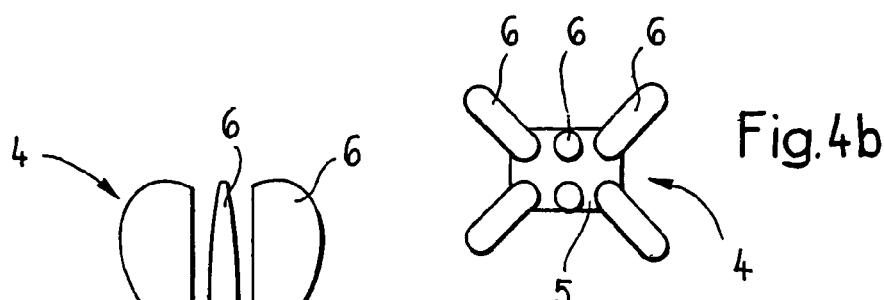
Figure 4C:
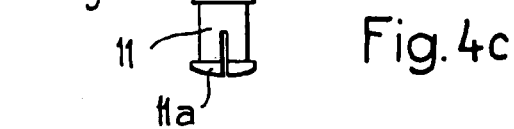
Figure 4D:
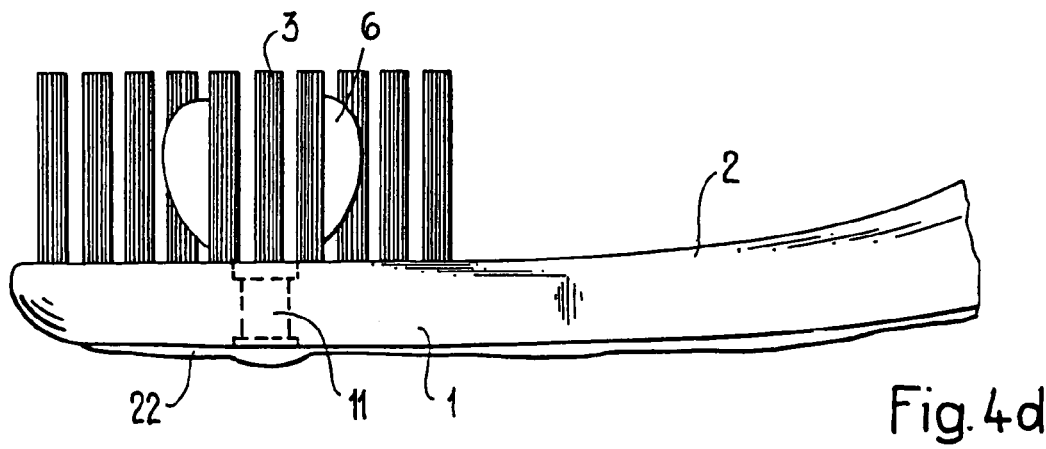
Figure 4E:
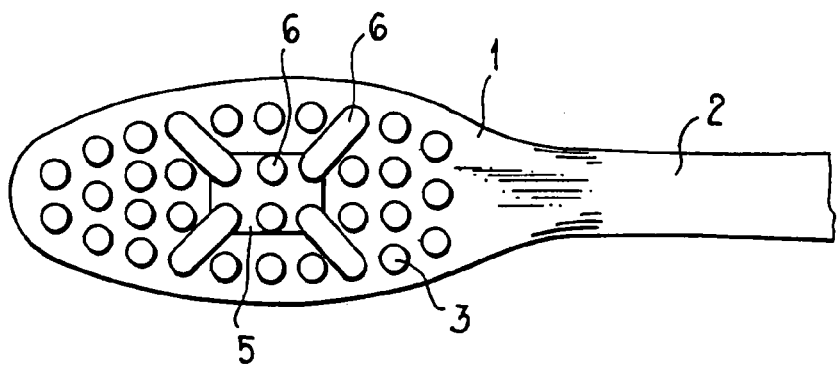
Figure 5A:
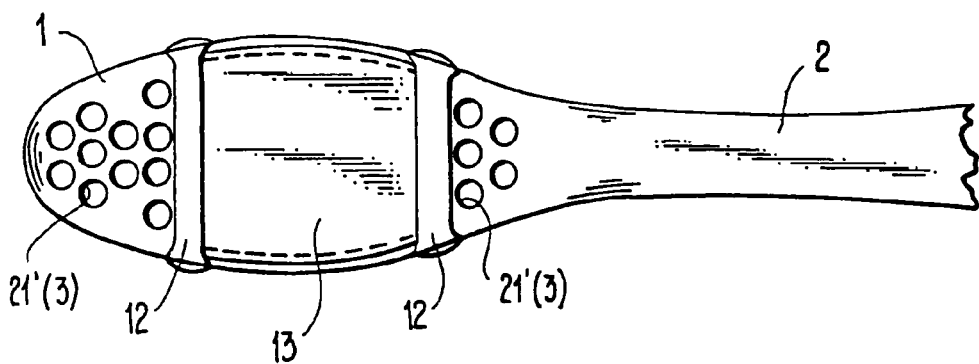
FIGS. 5a-e show views of a further toothbrush of which the additional part is fastened by a snap-fitting connection.
Figure 5B:
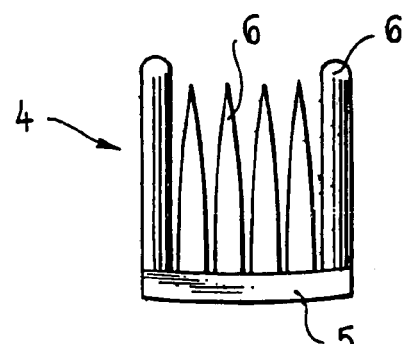
Figure 5C:
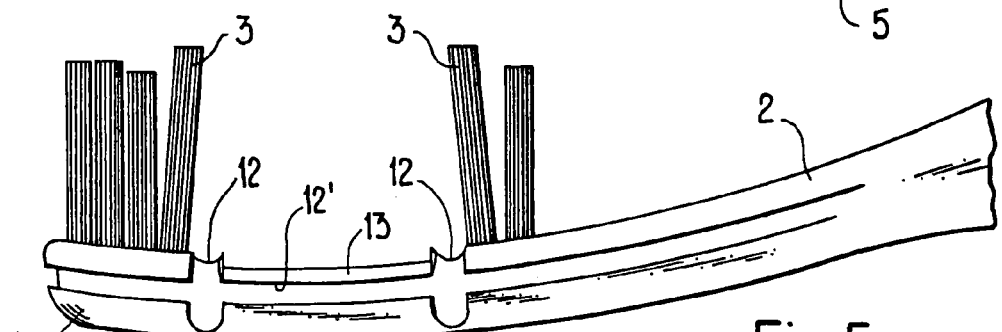
Figure 5D:
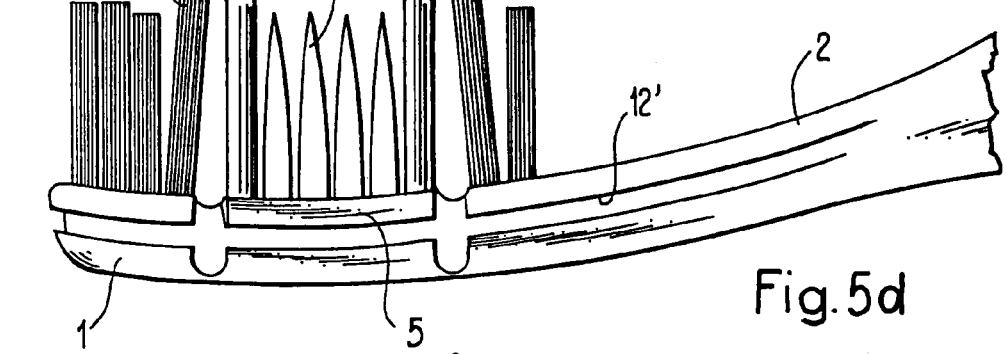
Figure 5E:
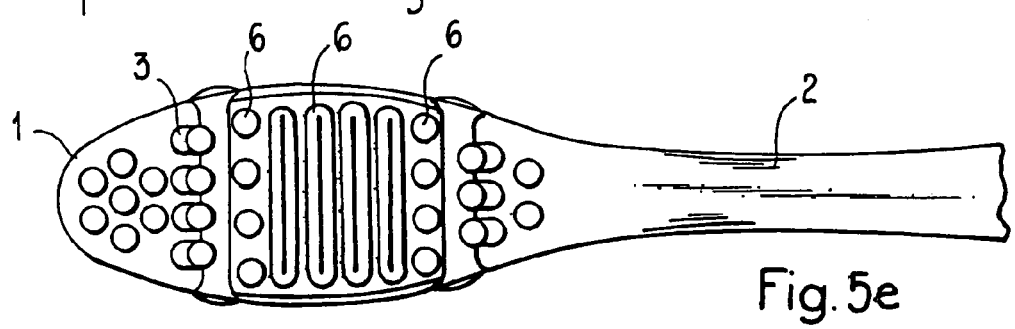

The additional part 4 of the toothbrush illustrated in FIGS. 4a-e is fastened in the center of the head part 1 by means of snap-fitting. The additional part 4 comprises a rectangular carrier element 5 with wing-like flexible cleaning elements 6 arranged at its corners. Two rod-like cleaning elements 6 are also located on the carrier element 5 (FIGS. 4b and c). As is illustrated in FIG. 4a, the head part 1 has a central hole 8'', through which a resiliently configured extension 11 on the carrier element 5 is plugged. The additional part 4 and head part 1 are connected to one another by a snap-fitting connection which, on account of the enlarged cross section at the bottom end 11a of the extension 11, cannot readily be released. The bristle arrangement of the conventional clusters of bristles 3 is configured such that the wing-like cleaning elements 6 are positioned between the conventional clusters of bristles 3, as is illustrated in FIGS. 4a and 4e. The additional part 4 is produced separately and then inserted into the head part 1 with the prepared bristle arrangement. It is thus also possible to realize structures of the flexible cleaning elements 6 which engage through the convention bristle arrangement, such as the diagonally arranged wing-like elements from FIGS. 4b-e or the fanned-out pin-like cleaning elements, oriented in different directions in space, from FIG. 8. For reasons of hygiene or esthetics, the underside of the head part 1 is covered by a layer 22 made of flexible material.

FIGS. 5a-e show a further example of a snap-fitting connection between the additional part 4 and the head part 1 of a toothbrush according to the invention. Within the bristle arrangement made of conventional clusters of bristles 3, the head part 1 has a prepared region 13 for accommodating the additional part 4. This region 13 comprises a depression with a groove 12 running on the border of the latter in each case, perpendicularly to the alignment of the handle 2, said groove 12 providing the head part 1 with a certain level of elasticity or resilient action, as do also the grooves 12' running on the lateral border of the head part. The prepared region 13 is slightly smaller than the basic surface area of the carrier element 5, with the result that the latter can be fitted into the region 13 in a clamping manner. As can be seen from the plan view in FIG. 5e, the additional part has both rod-like cleaning elements and sheet-like cleaning elements arranged transversely to the alignment of the handle 2.

FIGS. 6a-f show a further example of a toothbrush according to the invention, in this case a plug-on toothbrush for an electric teeth-cleaning unit. The conventional clusters of bristles 3 are fastened on a separate bristle plate 18 which, in the assembled state, is connected to the matching head part 1 of the toothbrush or a disc 23 which is fastened in a rotatable or pivotable manner thereon. The flexible cleaning elements 6, which are rod-like in this case, are fastened on a carrier element 5 which is slightly curved in plan view and has a sheet-like extension 16, which is oriented essentially perpendicularly to the alignment of the cleaning elements 6. The additional part 4 can be introduced, by way of said extension 16, into a correspondingly shaped groove 14 in the disc 23. Arranged in the center of the head part 1 and of the groove 14 is a round cutout 15, in which a corresponding mating element 17 on the extension 16 of the additional part 4 engages. The additional part 4 and head part 1 are thus connected to one another in a well-fitting and clamping manner. At its bottom end, the bristle plate 18 has a groove 19 by means of which the bristle plate 18 can be fastened on the disc 23 or the lateral extensions 23 thereof. In the embodiment illustrated, the additional part 4 is moved along by the disc 23. As an alternative, it is possible for the additional part 4 to be fastened directly on the head part 1 and not to rotate as well.

Figure 7A:
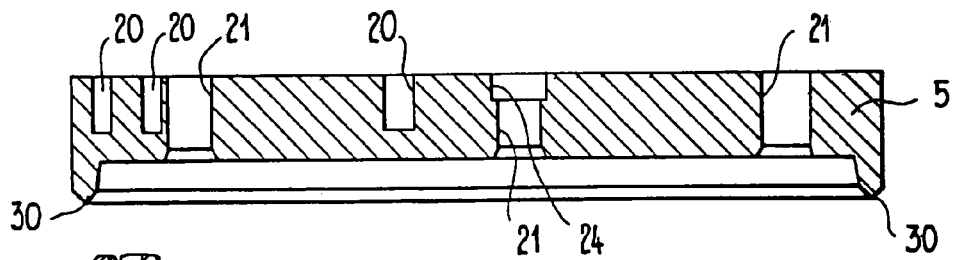
FIGS. 7a-e show the production of a toothbrush by AFT.
Figure 7B:
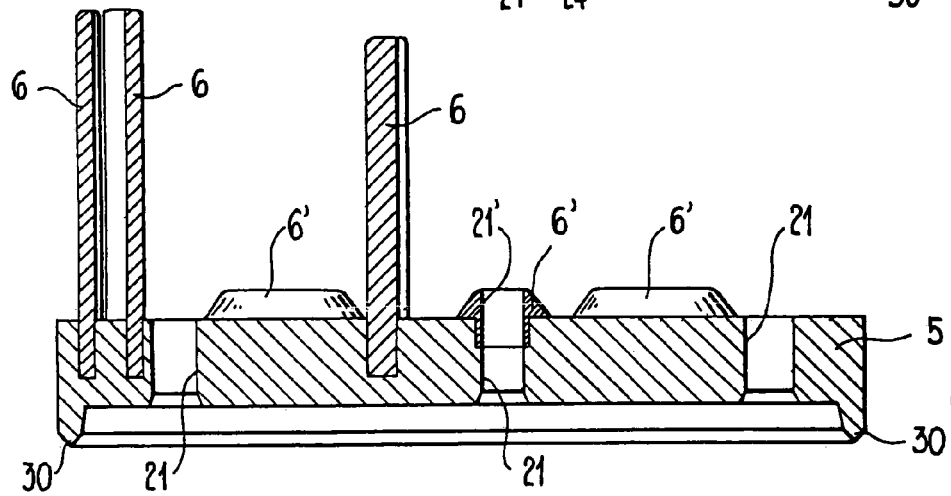
Figure 7C:
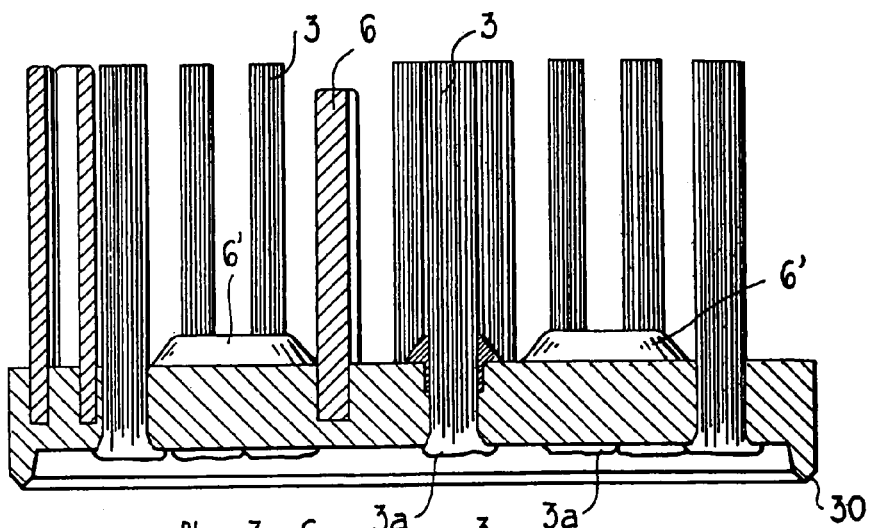
Figure 7D:
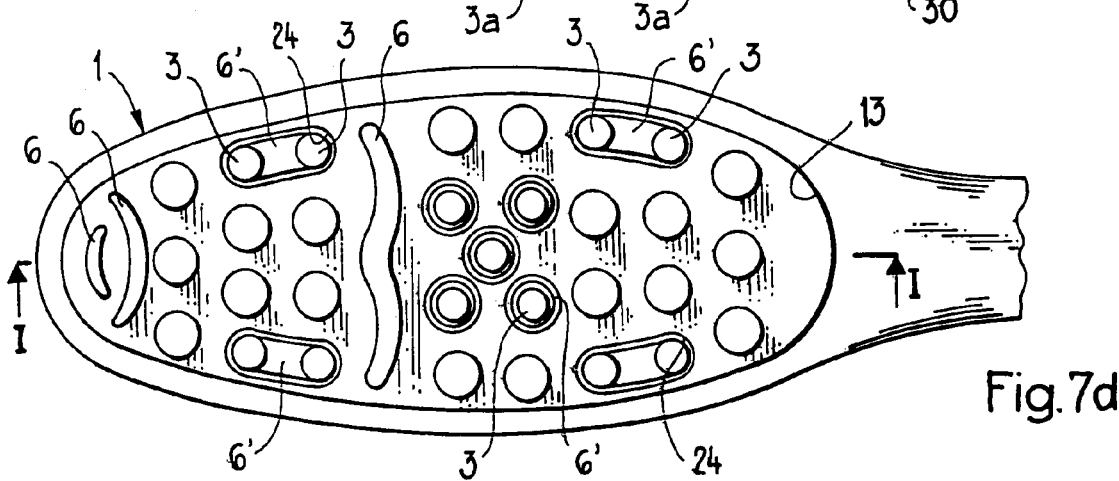
Figure 7E:
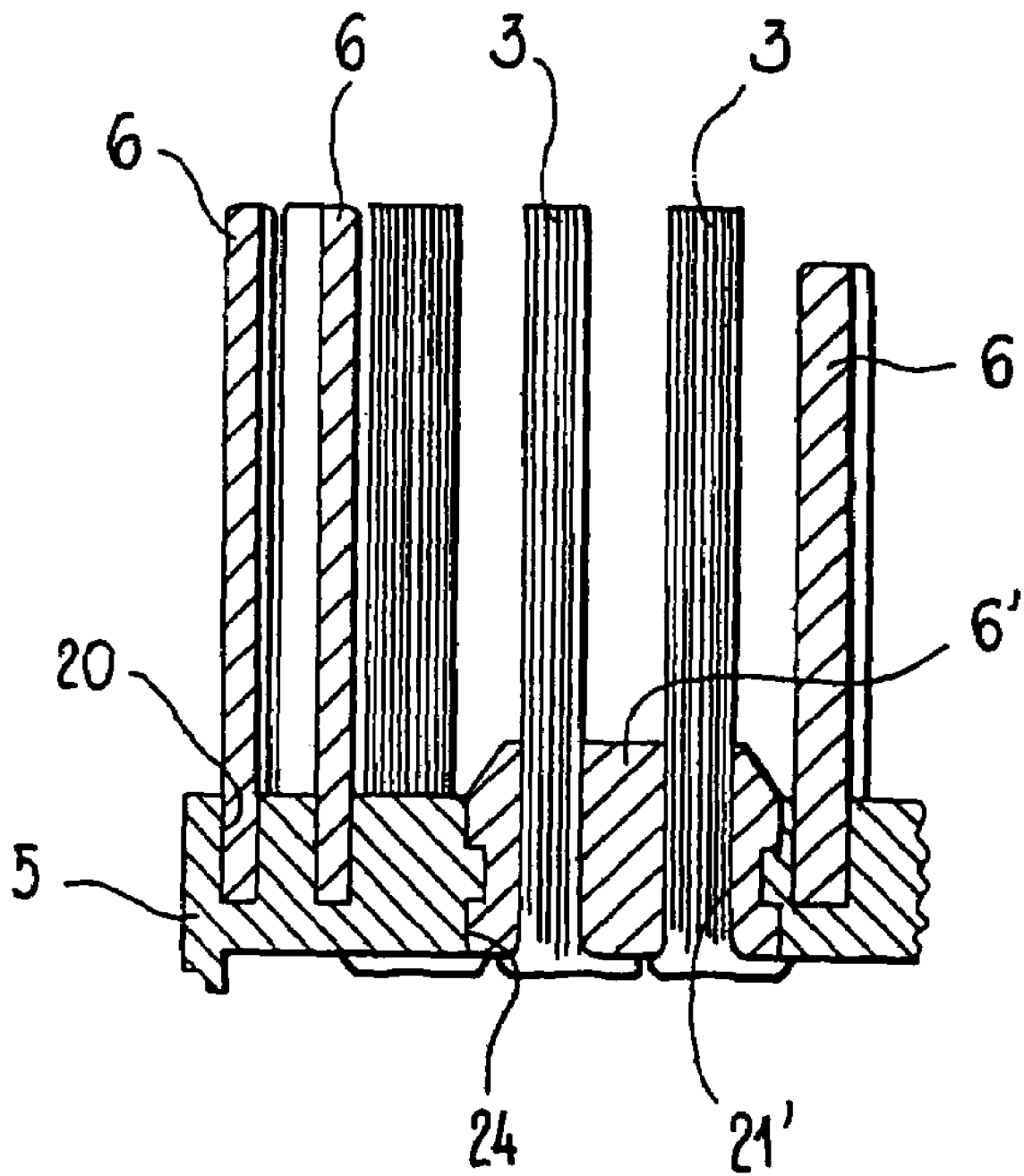
Figure 9A:
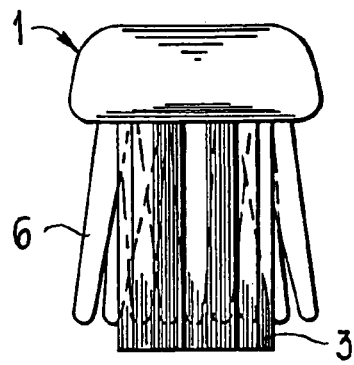
FIGS. 9a-f show views of a further toothbrush, of which the additional part is fastened on the head part with play.
Figure 9B:
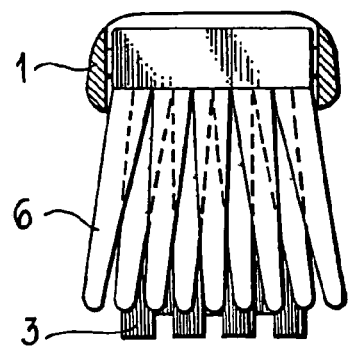
Figure 9C:
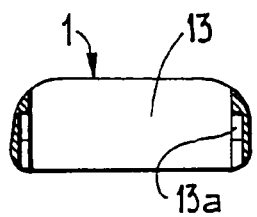
Figure 9D:
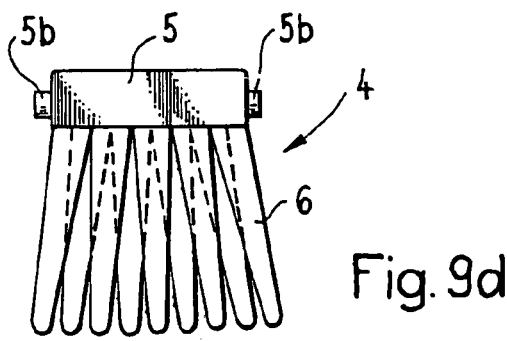
Figure 9E:
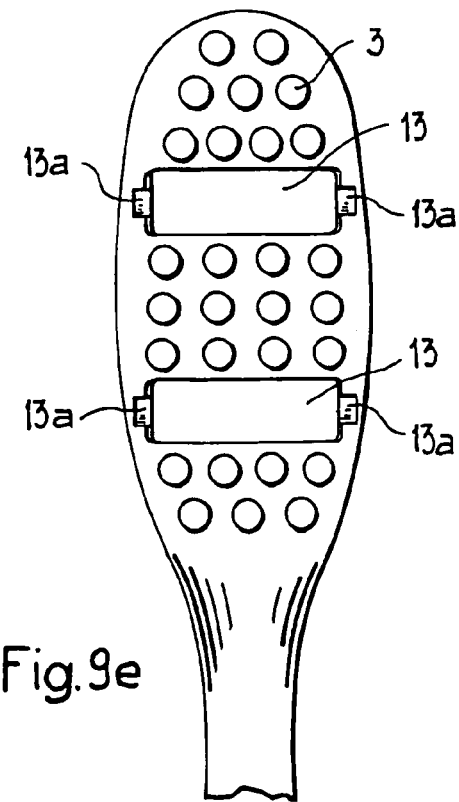
Figure 9F:
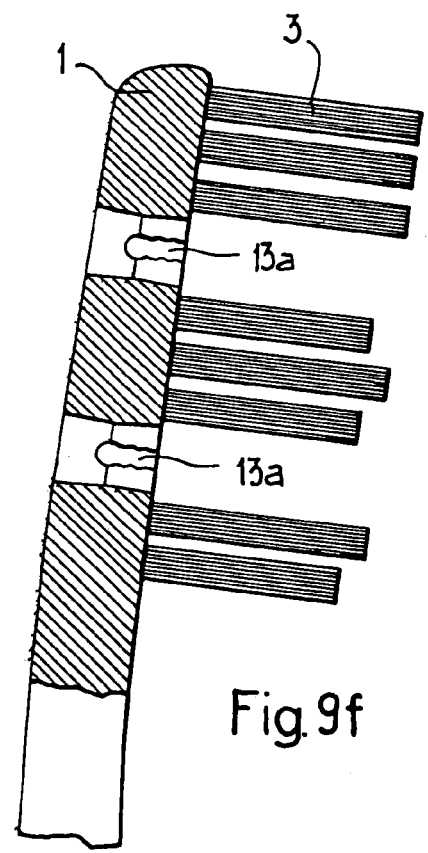

FIGS. 7a-e show an example of the production of a toothbrush by means of AFT technology. FIGS. 7a-c show sectional views of the carrier element 5 in various process stages, to be precise before being provided with flexible cleaning elements 6 and conventional clusters of bristles 3 (FIG. 7a), following the application of the flexible material (FIG. 7b) and following the application of the bristles (FIG. 7c). The outer shape of the carrier element 5 is adapted to the dimensions of a prepared region 13 in the form of a shallow cutout in the head part 1 of the toothbrush. The carrier element 5 has prepared regions 20, into which the flexible cleaning elements 6 are fitted, in particular molded. Furthermore, the carrier element 5 has cutouts 24, which are filled wholly or partially with flexible material 6', see also the detail from FIG. 7e. The carrier element 5 also contains holes 21, through which clusters of bristles 3 are plugged and are fastened on the rear side by virtue of their rear ends 3a being incipiently melted. The elastic material regions 6' have further holes 21' which likewise serve for accommodating clusters of bristles 3, which are fastened in the same way. The material regions 6' can accommodate one or more clusters of bristles 3. The clusters of bristles 3 anchored in the elastic material 6' are thus anchored or suspended in a particularly elastic manner. Further clusters of bristles 3 are fastened directly on the carrier element 5. The carrier element 5 fitted with clusters of bristles and the flexible structure 6, 6' is then inserted into the prepared region 13.

Figure 11A:
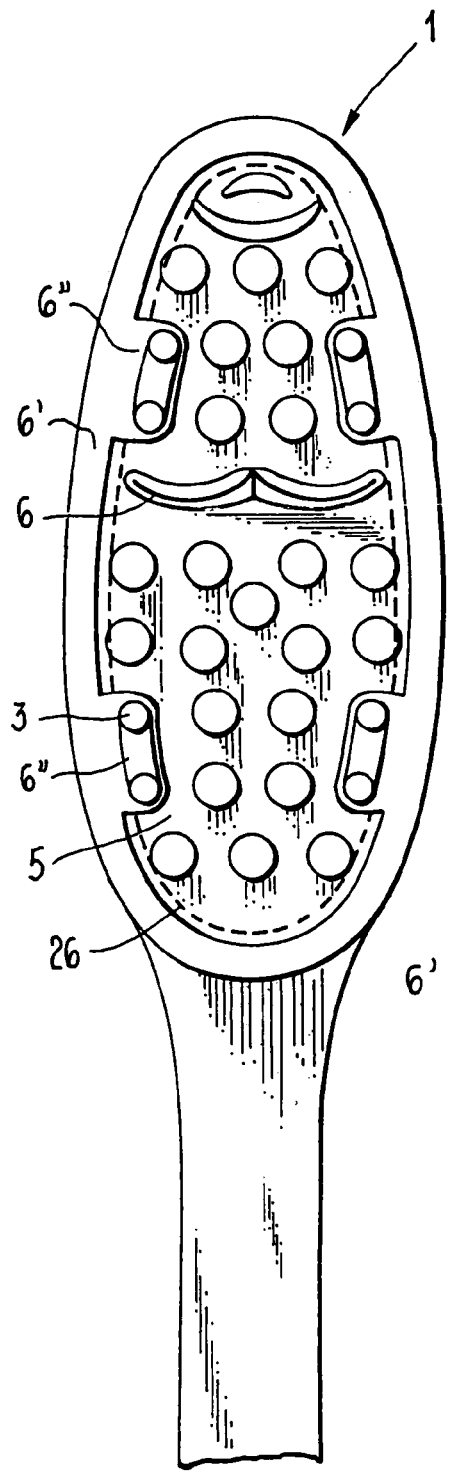
FIGS. 11a-c show views of a toothbrush with a lateral surround made of flexible material.
Figure 11B:
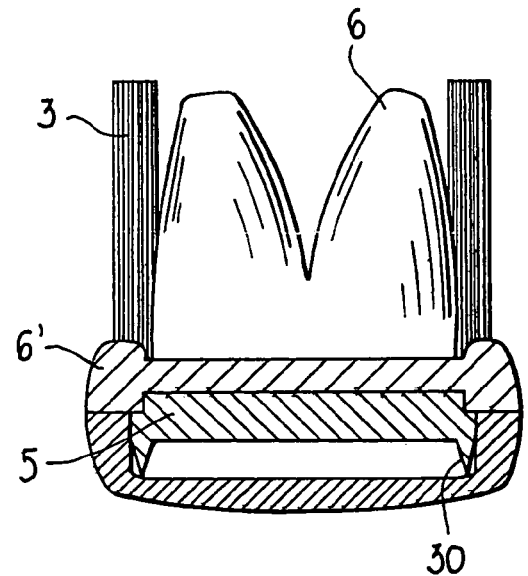

The edge 30 of the carrier element 5, this edge in the application case being directed towards the base of the cutout 13, is tapered, just as in the example from FIGS. 10 and 11. This tapering edge 30 serves, during ultrasonic welding for connection to the head part 1, as an energy concentrator and a material reservoir for material which is to be liquefied.

The AFT technology manages without anchors or clips for fastening the bristle filaments, which instead are welded directly on the carrier plate. This means that the width of a cluster of bristles is not determined by the anchor, with the result that it is also possible to realize finer structures, in particular also sheet-like bristle arrangements.

It is technically also possible, in the case of AFT, to prepare the bristle filaments for use before they are fitted on the carrier plate. The variant which is realized at present, however, is that where the bristles are only machined once they have been fitted on the carrier plate.

FIGS. 8*a-e* show a variant of the toothbrush from FIG. 4. The bristle arrangement made of conventional clusters of bristles 3 corresponds to FIG. 4. The additional part 4 has a plurality of pin-like cleaning elements 6 which diverge in the form of a star and engage through the conventional clusters of bristles 3 (FIGS. 8*d* and *e*). The fastening mechanism corresponds to FIG. 4. A layer 22 made of flexible material covers the underside of the head and handle parts 1, 2.

FIGS. 9*a-f* show a further example of a toothbrush according to the invention. The head part 1 has a prepared region 13 for the carrier element 5 of the additional part 4, said region being larger than the carrier element 5 itself. The region 13 is, for example, a hole which passes all the way through the head part 1, see sectional drawings from FIGS. 9*b*, *d* and *e*. The region 13 has two lateral grooves 13*a*, the shape of which is adapted to the shape of two lateral extensions 5*b* of the carrier element 5. The latter is inserted into the head part 1 and latches there. The play of the carrier element 5 within the region 13, which allows lateral displacement and/or a pivoting movement about the axis defined by the extensions 5*b*, results in a particular level of elasticity or resilient action of the additional part 4. The rear side of the head part 1, again, may be covered by a layer of soft material.

FIGS. 10*a-j* show a further example of a toothbrush produced by means of AFT. FIGS. 10*a-c* correspond to FIGS. 7*a-c* and each show the carrier plate 5 in various process stages. FIGS. 10*d-f* show the same carrier plate 5 in section along line I-I indicated in FIG. 10*a*. The centrally arranged flexible element 6 is sheet-like or sail-like and is undulating in plan view (FIG. 10*h*). As is illustrated in FIGS. 10*e* and *f*, the flexible structure comprises laterally integrally formed regions 6″ which, in the assembled state (FIG. 10*h*), bound the toothbrush head 1 laterally and terminate more or less flush with the outer contour of the head part. They serve, for example, as impact protection and/or for additionally massaging the gums. The regions 6″ likewise have holes 21′ for accommodating clusters of bristles 3, which are thus suspended in an elastic manner and are particularly compliant during cleaning.

The carrier element 5 provided with conventional bristles 3 and the flexible structure 6, 6′, 6″ is inserted into a cutout 13 in the brush head 1. The brush head 1 is illustrated in various views without the carrier element 5 in FIGS. 10*g* and *j* and with the carrier element 5 inserted in FIGS. 10*h* and *i*. On its lateral border, the brush head 1 or the cutout 13 has lateral openings 25, which are adapted to the lateral flexible regions 6″ previously molded on the carrier element 5.

The carrier element 5 is connected to the brush head 1 by means of ultrasonic welding. The welding surface 26 is indicated by dashed lines. In order to realize the welding, the carrier element has, on its bottom border, a welding border 26′ which, during assembly, rests on the base of the cutout 13, the contact surface defining the welding surface 26. The welding border 26′ melts under the influence of ultrasound, with the result that the two parts 5 and 1 are connected to one another.

Since elastomeric material can only be welded ultrasonically to a limited extent, the welding surface 26, as far as possible, is kept free of this material, for example as in the case of the toothbrush from FIG. 7 or, with only minimal interruptions, as in the case of the toothbrush from FIG. 10. The aim, in both cases, is to seal the cavity 28 between the carrier element 5 and head part 1 to the full extent, in order to prevent the ingress of water and germs. For this purpose, the injection point of the flexible material is preferably selected to be on the bristle-carrying front side of the carrier element 5, in order that no unnecessary material bridges reduce the size of the welding surface 26. If further flexible elements are provided on the head part 1, in particular on the rear side thereof, they are positioned such that they do not reduce the size of the welding surface 26. For example, these elements and the corresponding injection point are located fully within that region on the rear side of the head part 1 (not illustrated) which is defined by the welding surface 26. The entire contact surface between the head part 1 and carrier element 5 is preferably welded over at least 25%, particularly preferably along the periphery of the head (line 26).

In the example from FIG. 10, the flexible regions 6″ interrupt the welding surface 26, with the result that non-welded locations 27 are produced there. These are advantageously arranged on the side of the head part 1, while the longitudinally front and rear regions of the carrier element 5 are firmly welded to the head part 1. This ensures that the carrier element 5 is held securely since the front and rear regions are subjected to an extremely high level of loading by the cleaning movement and corresponding leverages.

The non-welded locations 27 are sealed by the flexible regions 6″ here in the manner of a sealing lip, with the result that only a very small amount of water, if any at all, can penetrate into the cavity 28. For a good sealing function, material with a Shore A hardness of 50 or less is preferably selected. Non-welded locations between the head part and carrier element may also be used specifically, in order to achieve a certain level of flexibility between the two hard components.

FIG. 11 shows various views of a further example of a toothbrush produced by AFT, in this case, with two sail-like flexible cleaning elements 6. The carrier element 5 is fully enclosed, around its periphery, by flexible material 6′, which, in the assembled state (plan-view illustration FIG. 11*a*) fully encloses the outer periphery of the head part 1 on the top side and serves as impact protection. In regions 6″, the soft material serves as a mount for lateral clusters of bristles 3 which are guided through the flexible material 6″.

Figure 11C:
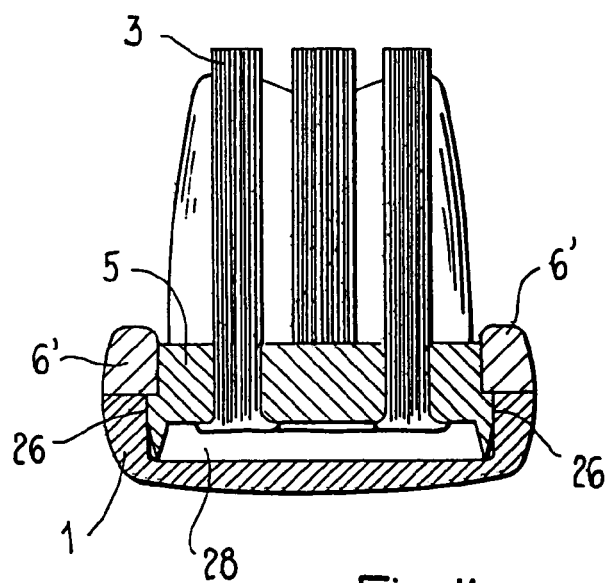

As can be gathered from FIG. 11*c*, the hard components (carrier element 5 and head part 1) come into contact with one another along a surface 26 beneath the soft component in the region 6′ and can be welded here by means of ultrasound. The welding surface 26 interrupted by the lateral regions 6″, although, as has been described above, a sufficient retaining action is achieved. The cavity 28 beneath the carrier element 5 is sealed by the flexible regions 6″ and the locations welded along the surface 26.

The method of welding and sealing the components which has been described above with reference to FIGS. 10 and 11 may also advantageously be used for other toothbrushes.

What is claimed is:

1. A carrier element for a toothbrush, comprising:
   a flexible structure attached to a plate-like carrier element having a front side and a rear side, the carrier element being of a harder material than the flexible structure, the carrier element comprising an edge-like welding border, bristle receiving cutouts are provided in the carrier element and/or the flexible structure, bristle filaments are guided through the bristle receiving cutouts, and rear ends of the bristle filaments are melted, welded or adhesively bonded on the rear side of the carrier element or the flexible structure.

2. The carrier element as claimed in claim 1, wherein the flexible structure comprises at least one flexible, non-bristle containing cleaning element.

3. The carrier element as claimed in claim 2, wherein the carrier element comprises at least one cleaning element receiving cutout extending at least partially through the carrier element in which said non-bristle containing cleaning element is anchored.

4. The carrier element as claimed in claim 2, wherein the non-bristle containing cleaning element comprises sheet-like elements that are arranged centrally on the carrier element.

5. The carrier element as claimed in claim 1, wherein the carrier element is formed to be inserted and welded into a carrier element receiving cutout of a head part of the toothbrush.

6. The carrier element as claimed in claim 1, wherein a welding border defining a welding surface between the carrier element and a head part of the toothbrush is kept free of the flexible component.

7. The carrier element as claimed in claim 1, wherein flexible regions interrupt a welding surface, with the result that non-welded locations are present.

8. The carrier element as claimed in claim 7, wherein the non-welded locations are produced on a lateral side.

9. The carrier element as claimed in claim 1, wherein the longitudinally front and rear regions of the carrier element are firmly welded to a head part of the toothbrush.

10. The carrier element as claimed in claim 1, wherein non-welded locations between a head part of the toothbrush and the carrier element are used specifically, in order to achieve a certain level of flexibility between the hard components of the carrier element and of the head part.

11. The carrier element as claimed in claim 1, wherein non-welded locations between a head part of the toothbrush and the carrier element are used in order that the head part and the carrier element can be moved in relation to one another.

12. The carrier element as claimed in claim 1, wherein the flexible structure and the carrier element are produced by multi-component injection molding and mated with a non-releasable connection.

13. The carrier element as claimed in claim 1, wherein an injection point for producing the flexible structure is located on the front side.

14. The carrier element as claimed in claim 1, wherein the flexible structure comprises natural or synthetic rubber.

15. The carrier element as claimed in claim 1, wherein the flexible structure comprises a thermoplastic elastomer.

16. The carrier element as claimed in claim 1, wherein the flexible structure has a Shore A hardness of less than 90.

17. The carrier element as claimed in claim 1, wherein at least one of the bristle receiving cutouts is arranged in the flexible structure and provided with bristle filaments that are anchored to the flexible structure in an elastic manner.

18. The carrier element as claimed in claim 1, further comprising bristle receiving cutouts arranged directly in the carrier element, the cutouts being provided with bristle filaments.

19. The carrier element as claimed in claim 1, wherein the flexible structure comprises regions arranged laterally on the carrier element, said regions terminating laterally with the outer contour of a head part of the toothbrush or projecting beyond the head part when the carrier element is attached to the head part.

20. A carrier element for a toothbrush, comprising:
a flexible structure attached to a plate-like carrier element having a front side and a rear side, the carrier element being of a harder material than the flexible structure, the flexible structure comprising at least one flexible, non-bristle containing cleaning element, bristle receiving cutouts are provided in the carrier element and/or the flexible structure, bristle filaments are guided through the bristle receiving cutouts, and rear ends of the bristle filaments are melted, welded or adhesively bonded on the rear side of the carrier element or the flexible structure.

21. A carrier element for a toothbrush, comprising:
a flexible structure attached to a plate-like carrier element having a front side and a rear side, the carrier element being of a harder material than the flexible structure, wherein the flexible structure comprises regions arranged laterally on the carrier element, bristle receiving cutouts are provided in the carrier element and/or the flexible structure, bristle filaments are guided through the bristle receiving cutouts, and rear ends of the bristle filaments are melted, welded or adhesively bonded on the rear side of the carrier element or the flexible structure.

22. A carrier element for a toothbrush, comprising:
a flexible structure attached to a plate-like carrier element having a front side and a rear side, the carrier element being of a harder material than the flexible structure, the flexible structure comprising at least one flexible, non-bristle containing cleaning element, the carrier element comprises at least one cleaning element receiving cutout extending at least partially through the carrier element, in which said non-bristle containing cleaning element is anchored, bristle receiving cutouts are provided in the carrier element and/or the flexible structure, bristle filaments are guided through the bristle receiving cutouts, and rear ends of the bristle filaments are melted, welded or adhesively bonded on the rear side of the carrier element or the flexible structure.

23. A toothbrush comprising a carrier element as claimed in claim 1.

24. A method for producing a carrier element comprising:
providing a carrier element having a front side and a rear side;
attaching a flexible structure to the carrier element, wherein the carrier element is made from a harder material than that of the flexible structure;
providing a plurality of bristle filaments and guiding them through bristle receiving cutouts in the carrier element and/or in the flexible structure; and
fastening rear ends of the bristles on a rear side of the carrier element and/or the flexible structure by melting, welding or adhesive bonding.

25. The method as claimed in claim 24, further comprising cutting and/or rounding the bristle filaments before fastening of the bristles to the carrier element and/or the flexible structure.

26. The method as claimed in claim 24, comprising producing the flexible structure and the carrier element by two-component injection molding.

27. The method as claimed in claim 24, comprising producing a non-releasable connection between the flexible structure and the carrier element.

28. The method as claimed in claim 24, further comprising providing an injection point of the flexible material on the front side of the carrier element.

29. A method for producing a toothbrush comprising a carrier element as claimed in claim 1 wherein the carrier element is non releasably connected to a head part of the toothbrush.

* * * * *